United States Patent [19]

Kubek

[11] Patent Number: 4,883,865
[45] Date of Patent: Nov. 28, 1989

[54] RECOVERY OF PRES2+S ANTIGEN

[75] Inventor: Dennis J. Kubek, Lansdale, Pa.

[73] Assignee: Merck & Co. Inc., Rahway, N.J.

[21] Appl. No.: 102,957

[22] Filed: Sep. 30, 1987

[51] Int. Cl.⁴ .......................... C07K 3/18; C07K 3/28
[52] U.S. Cl. .................................. 530/415; 530/412; 530/414; 530/418; 530/419; 530/420; 530/421; 530/422; 530/423; 530/424; 424/89; 435/68
[58] Field of Search .......................... 424/89; 435/68; 530/412, 414, 415, 418–424

[56] References Cited

U.S. PATENT DOCUMENTS

| | | | |
|---|---|---|---|
| 4,649,192 | 3/1987 | Wjnendaele et al. | 424/89 |
| 4,683,294 | 7/1987 | Wijnendaele et al. | 530/419 |
| 4,694,074 | 9/1987 | Uemura et al. | 435/68 |
| 4,707,542 | 11/1987 | Friedman et al. | 424/89 |
| 4,738,926 | 4/1988 | Hamada et al. | 435/68 |
| 4,742,158 | 5/1988 | Lehman et al. | 435/68 |
| 4,778,761 | 10/1988 | Miyanohara et al. | 435/68 |

FOREIGN PATENT DOCUMENTS 0112506  7/1984  European Pat. Off. ............. 424/89

OTHER PUBLICATIONS

Cheny et al., *J. Virol.* 60(2) 1986, pp. 337–344.
Einarsson et al., *J. Virol Methods* 8, 1984, pp. 233–241.
Neurnth et al., *Nature* 315, 1985, pp. 154–156.
Hamada et al., CA, vol. 104, 1986, p. #33032f.
Jensen et al., *PNAS* 80: 3035–3039 (83).

*Primary Examiner*—Garnette D. Draper
*Attorney, Agent, or Firm*—Donald J. Perrella; Hesna J. Pfeiffer

[57] ABSTRACT

A liquid phase containing preS2+S antigen is separated into two phases after which the desired antigen is concentrated, washed and adsorbed and desorbed from a fumed silica to produce a product that is purified and concentrated in antigen:protein ratio and that is suitable for final purification.

5 Claims, No Drawings

RECOVERY OF PRES2+S ANTIGEN

BACKGROUND OF THE INVENTION

The hepatitis B virus preS2 antigen gene linked in one contiguous reading frame to the hepatitis B virus surface antigen gene has been expressed in a transformed host. The expressed protein is useful as a vaccine for the treatment and prevention of hepatitis B virus-induced diseases and/or infections and in in vitro diagnostic systems. The purification of the expressed protein from either broken cell slurries or from cell supernatant liquids, however, has heretofore resulted in large losses in yield due to degradation of the antigen.

RECOVERY OF PRES2+S ANTIGEN

OBJECTS OF THE INVENTION

It is, therefore, an object of the present invention to provide a method for the recovery of preS2+S antigen in high yield. Another object is to provide a method that facilitates purification of the preS2+S antigen. These and other objects of the present invention will be apparent from the following description.

SUMMARY OF THE INVENTION

A liquid phase with or without solids containing preS2+S antigen is separated into two aqueous phases after which the desired antigen is adsorbed and desorbed from a fumed silica to produce a product purified in 50–100 fold (antigen:protein ratio) that is suitable for final concentration and purification.

DETAILED DESCRIPTION

The present invention relates to the recovery and purification of preS2+S antigen from broken cell slurries or cell supernatant liquids.

According to the present invention, the foregoing objects are achieved by a two-phase aqueous extraction of the preS2+S antigen coupled with adsorption to and desorbtion from fumed silica.

A broken cell slurry or a cell supernatant liquid is separated into two phases by adding to the broken cell slurry or cell supernatant liquid polyethylene glycol (PEG) and dextran. The PEG and dextran form two aqueous phases and the preS2+S antigen migrates to the upper PEG-containing layer. A surfactant preferably is present to increase the solubility of the antigen. A pH buffer and salts preferably are present to enhance the migration of the antigen into the PEG-containing layer.

A suitable PEG is PEG 3350 and a suitable dextran is Dextran T500. An example of a nonionic surfactant is Triton X-100. Examples of useful salts are NaCl and $K_2HPO_4$.

The broken cell slurry or cell supernatant liquid with the foregoing added ingredients is centifuged and the top phase is drawn off, diluted and filtered.

The filtrate is concentrated and diafiltered to remove PEG. Residual surfactant is removed and the antigen is adsorbed to fumed silica at slightly elevated pH and lowered temperature. The antigen is then eluted from the fumed silica, treated to remove residual silica, concentrated, diafiltered and sterile filtered.

The following example illustrates the present invention without, however, limiting the same thereto.

EXAMPLE

To an 8 ml slurry of broken yeast cells of strain CF42 containing 0.5% of Triton X-100 there is added 1 ml PBS (phosphate buffered saline), 0.7 g $K_2HPO_4$, 1 ml 5M NaCl, 6 ml of a 20% solution of PEG 3350 and 4 ml of a 20% solution of Dextran T500. The resulting mixture is centrifuged at 2500×g at 4° C. for 15 minutes. [Strain CF42 is a ura3 mutation of S. cerevisiae strain 2150-2-3 that was obtained from the collection of Dr. L. Hartwell of the University of Washington and diploidized by transforming with plasmid YCp50 HO [Jensen et al. P.N.A.S. USA 80: 3035–3039 (1983)]. A diploid strain was cured of the plasmid and designated CF42, (MATa/α, ade3, leu2-04, ura3)].

The antigen-containing PEG 3350 top phase (12–13ml) is separated and diluted 1:2 with PBS and filtered through a 0.2μ filter. The filtrate is concentrated and diafiltered with 10 volumes PBS to remove the PEG 3350 on an Amicon $10^5$ mw cutoff membrane. Residual Triton X-100 is removed with XAD-2 resin and the resin beads are then separated by filtration.

The filtrate is adsorbed to Aerosil 380 (having a surface of 380 $m^2/g$) at a pH of 7.5–7.6 and a temperature of 2°–8° C. for a period of 2.5 hours and then centrifuged at 2500×g at 4° C. for 15 minutes. The amount of Aerosil 380 that is used is determined from the formula: Weight (gm) Aerosil=0.0259×(Filtrate Vol In Ml)×$(A_{280}-A_{350})$ where $(A_{280}-A_{350})$ is the difference in absorbance at $\lambda_{280}$ and $\lambda_{350}$ of a 1:10 dilution of the filtrate. Therefore, the amount of Aerosil 380 added will be a function of cell breakage as well as removal of waste proteins, etc., during processing.

The antigen is eluted from the Aerosil 380 by the addition of 15 ml of borate buffer, pH 8.7, per g of Aerosil 380. This elution step is repeated once and the combined eluates are centrifuged 30 minutes at 11,000×g to remove Aerosil 380 fines, diafiltered with borate buffer on an Amicon $10^5$ mw cutoff membrane, and sterile filtered through a 0.22 μ filter. The antigen to protein ratio of preS2+S antigen in the filtrate in replicate runs was from 12–20% with antigen yields of from 30–65% based on total antigen indicating no significant degradation during processing.

What is claimed is:

1. A method of isolating a yeast-produced preS2+S antigen from a liquid phase comprising:
    forming the liquid phase into an upper preS2+S antigen-containing hydrophobic phase by addition of PEG, and a lower hydrophilic phase by addition of dextran,
    separating the upper liquid phase from the lower liquid phase,
    absorbing the antigen in the antigen-containing upper liquid phase on fumed silica,
    and desorbing the adsorbed antigen.

2. A method according to claim 1 wherein the desorbed antigen is diafiltered.

3. A method according to claim 2 wherein the antigen is diafiltered against borate buffer.

4. A method according to claim 2 wherein the antigen is sterile filtered following diafiltration.

5. A method according to claim 1 wherein the antigen is recovered without significant degradation in a yield of from about 30% to about 65%.

* * * * *